United States Patent
Pan et al.

(10) Patent No.: US 9,717,662 B2
(45) Date of Patent: Aug. 1, 2017

(54) ORAL CARE COMPOSITIONS

(71) Applicant: Colgate-Palmolive Company, New York, NY (US)

(72) Inventors: Long Pan, Cherry Hill, NJ (US); Venda Porter Maloney, Piscataway, NJ (US); Kristen Reale, Blairstown, NJ (US); Suman Chopra, Monroe, NJ (US); James G. Masters, Ringoes, NJ (US); Shaotang Yuan, East Brunswick, NJ (US); Laurence Du-Thumm, Princeton, NJ (US)

(73) Assignee: Colgate-Palmolive Company, New York, NY (US)

( * ) Notice: Subject to any disclaimer, the term of this patent is extended or adjusted under 35 U.S.C. 154(b) by 11 days.

(21) Appl. No.: 14/770,142

(22) PCT Filed: Mar. 15, 2013

(86) PCT No.: PCT/US2013/032391
§ 371 (c)(1),
(2) Date: Aug. 25, 2015

(87) PCT Pub. No.: WO2014/143019
PCT Pub. Date: Sep. 18, 2014

(65) Prior Publication Data
US 2016/0000666 A1    Jan. 7, 2016

(51) Int. Cl.
*A61Q 11/00* (2006.01)
*A61K 8/26* (2006.01)
*A61K 33/06* (2006.01)
*A61K 8/44* (2006.01)
*A61K 8/365* (2006.01)

(52) U.S. Cl.
CPC ........... *A61K 8/26* (2013.01); *A61K 8/365* (2013.01); *A61K 8/44* (2013.01); *A61Q 11/00* (2013.01)

(58) Field of Classification Search
USPC .............................. 424/49, 661, 662, 682, 52
See application file for complete search history.

(56) References Cited

U.S. PATENT DOCUMENTS

| | | |
|---|---|---|
| 3,538,230 A | 11/1970 | Pader et al. |
| 3,862,307 A | 1/1975 | DiGiulio |
| 4,108,979 A * | 8/1978 | Muhler ............. A61Q 11/00 424/49 |
| 4,146,605 A * | 3/1979 | Ritchey ............. A61K 8/21 424/49 |
| 4,340,583 A | 7/1982 | Wason |
| 4,645,662 A | 2/1987 | Nakashima et al. |
| 5,188,821 A | 2/1993 | Gaffar et al. |
| 5,192,531 A | 3/1993 | Gaffar et al. |
| 5,785,955 A | 7/1998 | Fischer |
| 7,897,799 B2 | 3/2011 | Pan et al. |
| 8,147,810 B2 | 4/2012 | Pan et al. |
| 8,257,689 B2 | 9/2012 | Pan |
| 2005/0207994 A1 * | 9/2005 | Sugiyama ............ A61K 8/26 424/49 |
| 2006/0198859 A1 | 9/2006 | Allef et al. |
| 2013/0022566 A1 | 1/2013 | Pan |
| 2013/0195773 A1 * | 8/2013 | Kindel ............. A23L 1/22075 424/49 |
| 2013/0224270 A1 | 8/2013 | Robinson et al. |
| 2014/0341820 A1 | 11/2014 | Maloney et al. |

FOREIGN PATENT DOCUMENTS

| | | |
|---|---|---|
| CN | 1850020 A | 10/2006 |
| JP | S60-184007 A | 9/1985 |
| JP | S61-155312 | 7/1986 |
| JP | S61-155313 | 7/1986 |
| JP | S61-155314 | 7/1986 |

OTHER PUBLICATIONS

Cummins 2009, "Dentin hypersensitivity: from diagnosis to a breakthrough therapy for everyday sensitivity relief." J. Clinical Dentistry 20(1):1-9.
International Search Report and Written Opinion in International Application No. PCT/US2013/032391, mailed Oct. 30, 2013.
Pappas et al., 2009, "Thermally resolved in site dynamic light scattering studies of zirconium(IV) complex formation," Crystal Growth & Design 9(12):5213-5219.
Thau et al., 1965, "A New Procedure for the Preparation of Polyethylene-Mineral Oil Gels" J. Soc. Cosmetic Chemists 16:359-363.
Written Opinion in International Application No. PCT/US2013/032391, mailed Feb. 11, 2015.

* cited by examiner

Primary Examiner — Lezah Roberts

(57) ABSTRACT

Described herein are oral care compositions comprising an effective amount of aluminum chlorohydrate suspended in a carrier for preventing, reducing or inhibiting dentinal hypersensitivity, the aluminum chlorohydrate exhibiting a SEC chromatogram having a SEC Peak 4 to Peak 3 intensity ratio of at least 7 and a Peak 4 intensity greater than a Peak 5 intensity; and methods of using the same.

21 Claims, No Drawings

ORAL CARE COMPOSITIONS

BACKGROUND

Conventionally, two approaches have been taken to treat or ameliorate tooth sensitivity. Under one approach, the chemical environment proximal to the nerve is altered by application of various agents, such that the nerve is not stimulated, or not stimulated as greatly. Known agents useful in this chemical approach, including potassium salts (such as potassium nitrate, potassium bicarbonate, potassium chloride) and strontium, zinc salts, and chloride salts.

The second approach involves the mechanical shield of the nerve by, e.g., blocking of the dentinal tubules wholly or partially with "tubule blocking agents." Agents that have been disclosed in the prior art include, e.g., cationic alumina, clays, water-soluble or water-swellable polyelectrolytes, oxalates, amorphous calcium phosphate, hydroxyapatite, maleic acid copolymers and polyethylene particles.

Nevertheless, there still exists a need in the art for an oral care composition, which upon use, provides enhanced prevention or reduction of tooth sensitivity and is formulated for application to the oral cavity in a convenient form for providing substantially immediate relief over a period of time.

SUMMARY

Some embodiments of the invention provide an oral care composition comprising an effective amount of aluminum chlorohydrate suspended in a carrier for preventing, reducing or inhibiting dentinal hypersensitivity, the aluminum chlorohydrate exhibiting a SEC chromatogram having a SEC Peak 4 to Peak 3 intensity ratio of at least 7 and a Peak 4 intensity greater than a Peak 5 intensity.

In some embodiments, the oral care composition is substantially anhydrous.

In some embodiments, the carrier is hydrophobic.

In some embodiments, the hydrophobic carrier comprises an ingredient selected from: a fatty acid ester of glycerol; an oil selected from a vegetable oil, a synthetic oil or a mineral oil; a wax; a silicone oil or fluid; an alkylene glycol, optionally propylene glycol; a polyalkylene glycol, optionally polyethylene glycol; and a combination of two or more thereof. Typically, the hydrophobic carrier comprises a $C_{6-12}$ fatty acid ester of glycerol.

In some embodiments, the aluminum chlorohydrate is present in an amount of from 0.01 wt % to 20 wt %, optionally from 0.1 wt % to 5 wt %, further optionally from 0.25 wt % to 1 wt %, of the total composition weight.

In some embodiments, the aluminum chlorohydrate has an aluminum to chloride molar ratio of from 0.3:1 to 3:1 and exhibits a SEC chromatogram having a SEC Peak 4 to Peak 3 intensity ratio of at least 16.

In some embodiments, the aluminum chlorohydrate exhibits a SEC chromatogram having a SEC Peak 4 to Peak 3 intensity ratio of at least 7 and a Peak 4 intensity greater than a Peak 5 intensity.

In some embodiments, the aluminum chlorohydrate has a SEC Peak 4 area of at least 50% of a total area of Peaks 1, 2, 3, 4, 5, and 6 in the SEC chromatogram.

In some embodiments, the aluminum chlorohydrate has a SEC Peak 4 area of 95 to 100% of the total area of Peaks 1, 2, 3, 4, 5, and 6 in the SEC chromatogram.

In some embodiments, wherein the aluminum chlorohydrate has a SEC Peak 3 area of less than about 10% of the total area of Peaks 1, 2, 3, 4, 5, and 6 in the SEC chromatogram.

In some embodiments, the aluminum chlorohydrate has no SEC Peak 3 area.

In some embodiments, the aluminum chlorohydrate has a SEC Peak 5 area of less than about 30% of the total area of Peaks 1, 2, 3, 4, 5, and 6.

In some embodiments, the aluminum chlorohydrate has no SEC Peak 5 area.

In some embodiments, the aluminum chlorohydrate has a SEC Peak 1 area of less than about 10% and a SEC Peak 2 area of less than about 10% of the total area of Peaks 1, 2, 3, 4, 5, and 6.

In some embodiments, the aluminum chlorohydrate has a SEC Peak 4 area of 95 to 100%, no SEC Peak 3 area, and no SEC Peak 5 area of a total area of Peaks 1, 2, 3, 4, 5, and 6 in the SEC chromatogram.

In some embodiments, the composition is a mouthrinse or a toothpaste.

Some embodiments of the invention provide a method of preventing, reducing or inhibiting dentinal hypersensitivity comprising applying an effective amount of the composition of the invention to the oral cavity of a subject in need thereof.

Some embodiments of the invention provide a method of occluding dentin tubules, comprising administering the composition of the invention to a subject in need thereof.

Some embodiments of the invention provide the use of aluminum chlorohydrate exhibiting a SEC chromatogram having a SEC Peak 4 to Peak 3 intensity ratio of at least 7 and a Peak 4 intensity greater than a Peak 5 intensity for the manufacture of a composition for preventing, reducing or inhibiting dentinal hypersensitivity.

DETAILED DESCRIPTION

Some embodiments of the invention provide an oral care composition comprising an effective amount of aluminum chlorohydrate suspended in a carrier for preventing, reducing or inhibiting dentinal hypersensitivity, the aluminum chlorohydrate exhibiting a SEC chromatogram having a SEC Peak 4 to Peak 3 intensity ratio of at least 7 and a Peak 4 intensity greater than a Peak 5 intensity.

In some embodiments, the aluminum chlorohydrate has an aluminum to chloride molar ratio of from 0.3:1 to 3:1 and exhibits a SEC chromatogram having a SEC Peak 4 to Peak 3 intensity ratio of at least 16.

In some embodiments, the aluminum chlorohydrate exhibits a SEC chromatogram having a SEC Peak 4 to Peak 3 intensity ratio of at least 7 and a Peak 4 intensity greater than a Peak 5 intensity.

In some embodiments, the aluminum chlorohydrate has a SEC Peak 4 area of at least 50% of a total area of Peaks 1, 2, 3, 4, 5, and 6 in the SEC chromatogram.

In some embodiments, the aluminum chlorohydrate has a SEC Peak 4 area of 95 to 100% of the total area of Peaks 1, 2, 3, 4, 5, and 6 in the SEC chromatogram.

In some embodiments, wherein the aluminum chlorohydrate has a SEC Peak 3 area of less than about 10% of the total area of Peaks 1, 2, 3, 4, 5, and 6 in the SEC chromatogram.

In some embodiments, the aluminum chlorohydrate has no SEC Peak 3 area.

In some embodiments, the aluminum chlorohydrate, when tested in aqueous solution, has a SEC Peak 5 area of less than about 30% of the total area of Peaks 1, 2, 3, 4, 5, and 6.

In some embodiments, the aluminum chlorohydrate has no SEC Peak 5 area.

In some embodiments, the aluminum chlorohydrate has a SEC Peak 1 area of less than about 10% and a SEC Peak 2 area of less than about 10% of the total area of Peaks 1, 2, 3, 4, 5, and 6.

In some embodiments, the aluminum chlorohydrate has a SEC Peak 4 area of 95 to 100%, no SEC Peak 3 area, and no SEC Peak 5 area of a total area of Peaks 1, 2, 3, 4, 5, and 6 in the SEC chromatogram.

In some embodiments, the aluminum chlorohydrate is made according to the methods disclosed in the Applicant's U.S. Pat. Nos. 8,257,689 and 8,147,810.

For example, in some embodiments the aluminum chlorohydrate is made by a method comprising the steps of:

I) heating an aqueous solution containing an aluminum salt having an aluminum to chloride molar ratio of about 0.3:1 to about 3:1, with a buffer agent, at a temperature of about 50° C. to about 95° C. to reflux for a period of time of about 1 hour to about 5 hours to obtain an aluminum salt solution; and II) adding an aqueous solution of an inorganic base to obtain an aluminum salt solution having an OH:Al molar ratio of about 2:1 to about 2.6:1 to obtain a pH adjusted aluminum salt solution having a pH of about 2 to about 5.

Such a method can produce an aluminum chlorohydrate, in combination with a buffer, having a high SEC peak 4 in aqueous solution. The composition is obtained by a stepwise procedure to neutralize aluminum chloride in a buffered solution using inorganic bases. In some embodiments, the aluminum chlorohydrate obtained by this stepwise procedure have an aluminum to chloride molar ratio of about 0.3:1 to about 3:1, the aluminum chlorohydrate has a SEC Peak 4 to Peak 3 intensity ratio of at least 7 and a Peak 4 intensity greater than a Peak 5 intensity in aqueous solution.

Buffers that can be used can be chosen from glycine, and betaine. The buffer to aluminum molar ratio in certain embodiments can be about 0.1:1 to about 3:1. In another embodiment, the buffer to aluminum molar ratio is about 0.5:1 to about 2:1. In another embodiment, the buffer to aluminum molar ratio is about 1:1 to about 1.5:1.

The compositions may be made in a variety of ways involving a stepwise procedure to neutralize aluminum chloride in a buffered solution using inorganic basic salts. The procedure generally includes the step of heating an aqueous solution containing an aluminum chloride compound, in combination with a buffer agent, at a temperature of about 50° C. to about 95° C. to reflux for a period of time of about 1 hour to about 5 hours. In one such embodiment, an aqueous solution containing an aluminum chloride compound is heated at a temperature of about 75° C. to about 95° C. to reflux for a period of time of about 3 hours to about 4 hours. In another such embodiment, an aqueous solution containing an aluminum chloride compound and a buffer agent is heated at a temperature of about 75° C. to about 95° C. to reflux for a period of time of about 3 hours to about 4 hours. In one embodiment, the temperature is about 85° C.

In some embodiments, the solution has a buffer agent to aluminum molar ratio of about 0.1:1 to about 3:1. To adjust the pH of the aluminum salt solution, an aqueous solution of an inorganic base is added to the heated solution to thereby obtain a pH adjusted aluminum salt solution having a hydroxide to aluminum molar ratio of about 1:1 to about 4:1, and a pH of about 2 to about 5. In one such embodiment, the hydroxide to aluminum molar ratio of about 2:1 to about 3:1. In another such embodiment, the hydroxide to aluminum molar ratio is about 2.1:1 to about 2.6:1.

The aluminum chlorohydrate has a SEC Peak 4 to Peak 3 intensity ratio of at least 7 and a Peak 4 intensity greater than a Peak 5 intensity in aqueous solution.

In one embodiment, an aqueous aluminum chloride salt solution is buffered with betaine monohydrate and held at about 50° C. to about 95° C. to reflux for a period time of about 1 to about 6 hours. To the heated solution, an aqueous solution of an inorganic base is added dropwise over a period of time of about 1 to about 3 hours while maintaining the aluminum-betaine solution at about 50° C. to about 95° C. to reflux. In one such embodiment, the solution has a betaine to aluminum molar ratio of about 1.1. In another such embodiment, the solution has a betaine to aluminum molar ratio of about 1.25.

In one embodiment, an aqueous solution containing an aluminum chloride compound is buffered with betaine monohydrate and held at about 75° C. to about 95° C. to reflux for a period of time of about 3 hours to about 4 hours. In another such embodiment, an aqueous solution of an inorganic base is added dropwise over a period of time of about 1 to about 3 hours while maintaining the aluminum-betaine solution at about 75° C. to about 95° C. to reflux. In another embodiment, an aqueous solution of an inorganic base is added over a period of time in a series of additions while maintaining the aluminum-betaine solution at about 75° C. to about 95° C. to reflux. In one such embodiment, the inorganic base is added in at least 3 additions. In another such embodiment, the inorganic base is added in at least 5 additions.

In another embodiment, an aqueous aluminum chloride solution is buffered with glycine and held at about 50° C. to about 95° C. to reflux for a period time of about 1 to about 6 hours. To the heated solution, an aqueous solution of an inorganic base is added dropwise over a period of time of about 1 to about 3 hours while maintaining the aluminum-glycine solution at about 50° C. to about 95° C. to reflux. In one such embodiment, the solution has an aluminum to glycine molar ratio of about 0.4. In another such embodiment, the solution has an aluminum to glycine molar ratio of about 0.8.

In another embodiment, an aqueous solution containing an aluminum chloride compound is buffered with glycine and held at about 75° C. to about 95° C. to reflux for a period of time of about 3 hours to about 4 hours. In another such embodiment, an aqueous solution of an inorganic base is added dropwise over a period of time of about 1 to about 3 hours while maintaining the aluminum-glycine solution at about 75° C. to about 95° C. to reflux. In another embodiment, an aqueous solution of an inorganic base is added over a period of time in a series of additions while maintaining the aluminum-glycine solution at about 75° C. to about 95° C. to reflux. In one such embodiment, the inorganic base is added in at least 3 additions. In another such embodiment, the inorganic base is added in at least 5 additions. In one embodiment, the inorganic base is calcium hydroxide. In one such embodiment, the addition of calcium hydroxide provides an aqueous solution having a $Ca(OH)_2$:glycine molar ratio of about 1.25:1 to about 1:1.

For the above methods, the aluminum chloride salt and inorganic base may be obtained from a variety of sources. In one embodiment, the aluminum chloride salt includes aluminum trichloride, aluminum chlorohexahydrate and aluminum dichlorohydrate. In one such embodiment, the aluminum chloride salt is aluminum chlorohexahydrate.

In one embodiment, the inorganic base can be at least one base chosen from metal hydroxides, calcium hydroxide, strontium hydroxide, sodium hydroxide, barium hydroxide, metal oxides, calcium oxide, strontium oxide, and barium oxide.

The aluminum chlorohydrate produced by these methods has high levels of low molecular weight Al species. The high levels of low molecular weight Al is reflected in a SEC trace that has an intense Peak 4, and low Peaks 1, 2, 3 and 5. The polymerization of the aluminum chlorohydrate in aqueous solutions and the correspondent gelation process were followed by monitoring the molecular weight profile of the polyoxohalides in time by SEC. The relative retention time ("Kd") for each of these peaks varies depending on the experimental conditions, but the peaks remain relative to each other. The peak intensities were obtained using an SEC chromatogram using the following parameters: Waters®600 analytical pump and controller, Rheodyne® 77251 injector, Protein-Pak® 125 (Waters) column, Waters 2414 Refractive Index Detector. 5.56 mM nitric acid mobile phase, 0.50 ml/min flow rate, 2.0 microliter injection volume. Data was analyzed using Water® Empower software (Waters Corporation, Milford, Mass.). The concentration of the aluminum chlorohydrate in solution does not affect the retention time in the machine.

The aluminum chlorohydrate salts have high levels of low molecular weight Al species, which is reflected in a SEC trace that has intense Peak 4 and low Peaks 1, 2, and 3. The levels of the species corresponding to these peaks may be estimated based on the following ratios (or percentages):

$$f_{Pi} = \frac{Pi}{\sum Pj} \quad i = 1, 2, 3, 4, 5; \quad j = 2, 3, 4, 5$$

where $f_{Pi}$ is the fraction of peak i, and Pi or Pj are the intensity of peaks Pi or Pj, respectively. The amount of low molecular weight Al species will be correlated with the fraction, $f_{P4}$, or percentage, $f_{P4} \times 100$, of SEC-Peak 4. In brief, a preferred aluminum chlorohydrate salt would have a very low $f_{P1}$, $f_{P2}$, $f_{P3}$, and/or $f_{P5}$, and a high $f_{P4}$.

In one embodiment, an aluminum chlorohydrate salt, in aqueous solution, exhibits a SEC profile wherein the SEC Peak 4 to Peak 3 intensity ratio is at least 7. In such embodiments, the percentage of SEC Peak 4 of a total area of Peaks 1, 2, 3, 4, 5, and 6 in the SEC chromatogram is: at least 50%; at least 60%; at least 70%; at least 80%; at least 90%, or 95 to 100%. In another such embodiment, the SEC Peak 4 area is 100%.

In another embodiment, the aluminum chlorohydrate salt, in aqueous solution, exhibits a SEC profile wherein the SEC Peak 4 to Peak 3 intensity ratio is at least 7 and exhibits low percentage of SEC Peak 3. In such embodiments, the composition has the percentage of SEC Peak 3 area of a total area of Peaks 1, 2, 3, 4, 5, and 6 in the SEC chromatogram is: less than about 10%; less than about 5%; less than about 2%; less than about 1%; less than about 0.9%; less than about 0.8%; less than about 0.7%; less than about 0.6%; of less than about 0.5%; less than about 0.4%; less than about 0.3%; less than about 0.2%; or less than about 0.1%. In another such embodiment, the aluminum chlorohydrate salt has no SEC Peak 3 area.

In another embodiment, the aluminum chlorohydrate salt, in aqueous solution, exhibits a SEC profile wherein the SEC Peak 4 to Peak 3 intensity ratio is at least 7 and exhibits low percentages of SEC Peak 5. In such embodiments, the percentage of SEC Peak 5 area of a total area of Peaks 1, 2, 3, 4, 5, and 6 in the SEC chromatogram is: less than about 30%; less than about 20%; less than about 10%; less than about 5%; or less than about 1%. In another such embodiment, the aluminum chlorohydrate salt has no SEC Peak 5 area.

In another embodiment, the aluminum chlorohydrate salt, in aqueous solution, exhibits a SEC profile wherein the SEC Peak 4 to Peak 3 ratio is at least 7, and exhibits a low percentage of SEC Peak 1 and a low percentage of SEC Peak 2. In such embodiment, the percentage of SEC Peak 1 area of a total area of Peaks 1, 2, 3, 4, 5, and 6 in the SEC chromatogram is: less than about 10%; a SEC Peak 1 area less than about 5%; less than about 2%; less than about 1%; less than about 0.9%; less than about 0.8%; of less than about 0.7%; less than about 0.6%; less than about 0.5%; less than about 0.4%; less than about 0.3%; less than about 0.2%; or less than about 0.1%. In another embodiment, the aluminum chlorohydrate salt has no SEC Peak 1 area. In another embodiment, the percentage of SEC Peak 2 area of a total area of Peaks 1, 2, 3, 4, 5, and 6 in the SEC chromatogram is: less than about 10%; less than about 5%; less than about 2%; less than about 1%; less than about 0.9%; less than about 0.8%; less than about 0.7% ; less than about 0.6%; less than about 0.5%; less than about 0.4%; less than about 0.3%; less than about 0.2%; or less than about 0.1%. In another embodiment, the aluminum chlorohydrate salt has no SEC Peak 2 area.

In some embodiments, the oral care composition is substantially anhydrous.

As used herein, the term "substantially anhydrous" means no water is intentionally added to the composition. However, trace amounts of water that may be introduced via other ingredients or processing may exist, but only in amounts that will not prematurely trigger the activity of the active agent(s) in the composition, and/or reduce the stability of the composition. For example the maximum water content of the composition may be 3 wt %, or 2 wt % or 1 wt %, each based on the weight of the composition.

In some embodiments, the carrier is hydrophobic. In some embodiments, the hydrophobic carrier comprises an ingredient selected from: a fatty acid ester of glycerol; an oil selected from a vegetable oil, a synthetic oil or a mineral oil; a wax; a silicone oil or fluid; an alkylene glycol, optionally propylene glycol; a polyalkylene glycol, optionally polyethylene glycol; and a combination of two or more thereof. Typically, the hydrophobic carrier comprises a $C_{6-12}$ fatty acid ester of glycerol.

Medium chain triglycerides (MCTs) are preferred as the hydrophobic carrier. MCTs are typically about 6 to about 12 carbons in length. MCTs can be vegetable oils. Caprylic/capric triglyceride is a non-limiting example of an MCT preferred for use in the invention.

In some embodiments of the invention, the hydrophobic carrier is capable of suspending the aluminum chlorohydrate particles without substantial solubilization of such particles. Examples of suitable hydrophobic carriers are medium-chain triglycerides (MCTs), propylene glycol, polyethylene glycol, silicone fluid, castor oil, and mixtures thereof. Other solvents that are capable of solubilizing the aluminum chlorohydrate optionally may be present in the composition, provided that such a solvent does not adversely affect the efficacy of the composition, e.g. treatment of dentinal hypersensitivity.

MCTs are medium-chain (6 to 12 carbons) fatty acid tri-esters of glycerol, typically in the form of an oil. These oils can be prepared synthetically by well-known techniques, or can be obtained from natural sources by known techniques of thermal or solvent fractionation of suitable natural oils, such as palm oil or coconut oil, to yield fractions rich in the desired triglycerides. An exemplary low-melting, low molecular weight triglyceride oil is a low molecular weight fraction of coconut or palm oil which is rich in mixed esters of caprylic (octanoic) and capric (decanoic) acids. Such oil is commercially available as Miglyol 812 from SASOL GmbH Germany, CRODAMOL GTCC-PN from Croda Inc. of Parsippany, N.J., or Neobees M-5 oil from PVO International, Inc., of Boonton, N.J. Coconut oil is composed of approximately 66% medium-chain triglycerides. Other rich sources of MCTs include palm kernel oils and camphor tree drupes. The fatty acids found in MCTs are medium-chain fatty acids. The medium-chain fatty acids (and the corresponding number of carbons) found in MCTs are caproic acid (C6), caprylic acid (C8), capric acid (C10) and lauric acid (C12). In another embodiment the approximate ratios of these fatty acids in commercial MCT products derived from coconut oil are 2(C6):55(C8):42(C10):1(C12).

In some embodiments, the aluminum chlorohydrate is present in an amount of from 0.01 wt % to 20 wt %, optionally from 0.1 wt % to 5 wt %, further optionally from 0.25 wt % to 1 wt %, of the total composition weight.

In some embodiments, the composition is a mouthrinse or a toothpaste.

Some embodiments of the invention provide a method of preventing, reducing or inhibiting dentinal hypersensitivity comprising applying an effective amount of the composition of the invention to the oral cavity of a subject in need thereof.

Some embodiments of the invention provide a method of occluding dentin tubules, comprising administering the composition of the invention to a subject in need thereof.

Some embodiments of the invention provide the use of aluminum chlorohydrate exhibiting a SEC chromatogram having a SEC Peak 4 to Peak 3 intensity ratio of at least 7 and a Peak 4 intensity greater than a Peak 5 intensity for the manufacture of a composition for preventing, reducing or inhibiting dentinal hypersensitivity.

In some embodiments, the aluminum chlorohydrate is in the form of particles that are suspended in the hydrophobic carrier. In some embodiments, the hydrophobic carrier comprises from 5 to 99 wt % of the total composition weight. In other embodiments, the hydrophobic carrier comprises from 30 to 80 wt % of the total composition weight. In other embodiments, the hydrophobic carrier comprises from 70 to 75 wt % of the total composition weight.

The compositions of the present invention can be in any form that when administered will be effective in inhibiting, reducing or preventing (collectively referred to herein as "treating") dentinal hypersensitivity.

The compositions of the present invention can be administered by any suitable means known in the art. In some embodiments, an effective amount of aluminum chlorohydrate suspended in a hydrophobic carrier is administered to the oral cavity of a subject in need thereof.

Some embodiments of the oral care composition of the invention comprise a fluoride ion source. In some embodiments, the fluoride ion source is selected from: stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and a combination of two or more thereof. In some embodiments, the fluoride ion source is present in an amount of 0.01 wt % to 2 wt % of the total composition weight.

In some embodiments, the compositions may further include one or more fluoride ion sources, e.g., soluble fluoride salts. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as combinations thereof.

In certain embodiments, the oral care composition of the invention may contain a source of fluoride ions or fluorine-providing ingredient in amounts sufficient to supply 25 ppm to 25,000 ppm of fluoride ions, generally at least 500 ppm, e.g., 500 to 2000 ppm, e.g., 1000 to 1600 ppm, e.g., 450 ppm. The appropriate level of fluoride will depend on the particular application. A mouthrinse or mouthwash, for example, would typically have 100 to 250 ppm fluoride. A toothpaste for general consumer use would typically have 1000 to 1500 ppm, with pediatric toothpaste having somewhat less. A dentifrice or coating for professional application could have as much as about 5,000 or even about 25,000 ppm fluoride.

Fluoride ion sources may be added to the compositions of the invention at a level of 0.01 wt % to 10 wt % in one embodiment or 0.03 wt % to 5 wt %, and in another embodiment 0.1 wt % to 1 wt % by weight of the composition in another embodiment. Weights of fluoride salts to provide the appropriate level of fluoride ion will obviously vary based on the weight of the counter ion in the salt.

In some embodiments, the oral care composition further comprises an abrasive. In some embodiments, the abrasive is selected from sodium bicarbonate, calcium phosphate (e.g., dicalcium phosphate dihydrate), calcium sulfate, precipitated calcium carbonate, silica (e.g., hydrated silica), iron oxide, alumina (e.g., coated alumina), perlite, zirconium silicate, a plastic particle, e.g., polyethylene, and a combination of two or more thereof. In some embodiments, the abrasive is present in the amount of 15 wt % to 70 wt % of the total composition weight.

In some embodiments, the compositions of the present invention may comprise a calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4 \cdot 2H_2O$, also sometimes referred to herein as DiCal) or calcium pyrophosphate. Some embodiments may include one or more additional abrasives, for example silica abrasives such as precipitated silicas having a mean particle size of up to about 20 microns, such as Zeodent 115®, marketed by J. M. Huber. Other useful abrasives also include sodium metaphosphate, potassium metaphosphate, aluminum silicate, calcined alumina, bentonite or other siliceous materials, or combinations thereof.

The silica abrasive polishing materials useful herein, as well as the other abrasives, generally have an average particle size ranging between about 0.1 and about 30 microns, about between 5 and about 15 microns. The silica abrasives can be from precipitated silica or silica gels, such as the silica xerogels described in U.S. Pat. No. 3,538,230, to Pader et al. and U.S. Pat. No. 3,862,307, to Digiulio, both incorporated herein by reference. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340,583, to Wason, incorporated herein by reference.

In certain embodiments, the silicas are colloidal particles having an average particle size of about 3 microns to about 12 microns, and about 5 to about 10 microns.

In particular embodiments, the abrasive materials comprise a large fraction of very small particles, e.g., having a d50<5 microns, for example, small particle silica (SPS) having a d50 of about 3 to about 4 microns, for example Sorbosil AC43® (Ineos). Such small particles are particularly useful in formulations targeted at reducing hypersensitivity. The small particle component may be present in combination with a second larger particle abrasive. In certain embodiments, for example, the formulation comprises about 3 to about 8% SPS and about 25 to about 45% of a conventional abrasive.

Low oil absorption silica abrasives particularly useful in the practice of the invention are marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of 29% by weight averaging about 7 to about 10 microns in diameter, and an oil absorption of less than about 70 cc/100 g of silica is an example of a low oil absorption silica abrasive useful in the practice of the present invention. The abrasive is present in the oral care composition of the present invention at a concentration of 10 to 60 wt %, in other embodiment 20 to 45 wt %, and in another embodiment 30 to 50 wt %.

The compositions useful in the invention may contain anionic surfactants. The anionic surfactant may be present in an amount which is effective, e.g., >0.01 wt % of the composition, but not at a concentration which would be irritating to the oral tissue, e.g., <10 wt %, and optimal concentrations depend on the particular formulation and the particular surfactant. For example, concentrations used or a mouthwash are typically on the order of one tenth that used for a toothpaste. In one embodiment, the anionic surfactant is present in a toothpaste at from 0.3 to 4.5 wt %, e.g., about 1.5 wt %.

The compositions of the invention may optionally contain mixtures of surfactants, comprising anionic surfactants and other surfactants which may be anionic, cationic, zwitterionic or nonionic. Generally, surfactants are those which are reasonably stable throughout a wide pH range.

In a particular embodiment, the composition comprises sodium lauryl sulfate.

The surfactant or mixtures of compatible surfactants can be present in the compositions of the present invention in 0.1 to 5.0 wt %, in another embodiment 0.3% to 3.0 wt % and in another embodiment 0.5% to 2.0 wt % based on the total composition.

Some embodiments of the oral care composition of the invention comprise an anionic surfactant selected from:
a. water-soluble salts of higher fatty acid monoglyceride monosulfates (e.g., the sodium salt of the monosulfated monoglyceride of hydrogenated coconut oil fatty acids such as sodium N-methyl N-cocoyl taurate, sodium cocomono-glyceride sulfate),
b. higher alkyl sulfates, e.g., sodium lauryl sulfate,
c. higher alkyl-ether sulfates, e.g., of formula $CH_3(CH_2)_m CH_2(OCH_2CH_2)_n OSO_3X$, wherein m is 6-16, e.g., 10, n is 1-6, e.g., 2, 3 or 4, and X is Na or K (for example sodium laureth-2 sulfate $(CH_3(CH_2)_{10}CH_2 (OCH_2CH_2)_2 OSO_3Na)$),
d. higher alkyl aryl sulfonates (such as sodium dodecyl benzene sulfonate (sodium lauryl benzene sulfonate)),
e. higher alkyl sulfoacetates (such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate),
f. and mixtures thereof.

By "higher alkyl" is meant, e.g., $C_{6-30}$ alkyl. In particular embodiments, the anionic surfactant is selected from sodium lauryl sulfate and sodium ether lauryl sulfate. In some embodiments, the anionic surfactant is present in an amount of from 0.3 wt % to 4.5 wt % based on the total weight of the composition.

Some embodiments of the oral care composition of the invention may further comprise at least one humectant. Optionally, the humectant may be selected from glycerin, sorbitol, xylitol and combinations thereof.

Within certain embodiments of the oral compositions, it is also desirable to incorporate a humectant to prevent the composition from hardening upon exposure to air. Certain humectants can also impart desirable sweetness or flavor to dentifrice compositions. The humectant, on a pure humectant basis, generally includes from 15 to 70 wt % in one embodiment or from 30 to 65 wt % in another embodiment by weight of the oral care composition.

Suitable humectants include edible polyhydric alcohols such as glycerine, sorbitol, xylitol, propylene glycol as well as other polyols and mixtures of these humectants. Mixtures of glycerine and sorbitol may be used in certain embodiments as the humectant component of the toothpaste compositions herein.

Some embodiments of the oral care composition of the invention may further comprise at least one polymer. Optionally, the at least one polymer may be selected from a polyethylene glycol, a polyvinylmethyl ether maleic acid copolymer, a polysaccharide (e.g., a cellulose derivative, for example carboxymethyl cellulose, or a polysaccharide gum, for example xanthan gum or carrageenan gum), and a combination of two or more thereof.

Some embodiments of the oral care composition of the invention may further comprise gum strips or fragments. Some embodiments of the oral care composition of the invention may further comprise flavoring, fragrance and/or coloring.

Some embodiments of the oral care composition of the invention may further comprise comprising an antibacterial agent selected from a halogenated diphenyl ether (e.g. triclosan), a herbal extract and an essential oil (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), a bisguanide antiseptics (e.g., chlorhexidine, alexidine or octenidine), a quaternary ammonium compound (e.g., cetylpyridinium chloride (CPC), benzalkonium chloride, tetradecylpyridinium chloride (TPC), N-tetradecyl-4-ethylpyridinium chloride (TDEPC)), a phenolic antiseptic, hexetidine, octenidine, sanguinarine, povidone iodine, delmopinol, salifluor, a metal ion (e.g., zinc salts, for example, zinc citrate, stannous salts, copper salts, iron salts), sanguinarine, propolis and an oxygenating agent (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, a nicin preparation, a chlorite salt; and a combination of two or more thereof.

Some embodiments of the oral care composition of the invention further comprise an antibacterial agent in an amount of 0.01 to 5 wt % of the total composition weight. Some embodiments further comprise triclosan in an amount of 0.01 to 1 wt % of the total composition.

Some embodiments of the oral care composition of the invention further comprise a source of calcium and phosphate selected from (i) calcium-glass complexes, e.g., calcium sodium phosphosilicates, and (ii) calcium-protein complexes, e.g., casein phosphopeptide-amorphous calcium phosphate. Other embodiments of the oral care composition of the invention comprise a soluble calcium salt, e.g., selected from calcium sulfate, calcium chloride, calcium nitrate, calcium acetate, calcium lactate, and combinations thereof.

Yet further embodiments of the oral care composition of the invention comprise an orally acceptable potassium salt, e.g., potassium nitrate or potassium chloride, in an amount effective to reduce dentinal sensitivity. Some embodiments comprise from 0.1% to 7.5 wt % of an orally acceptable potassium salt, e.g., potassium nitrate and/or potassium chloride, based on the weight of the composition.

Some embodiments of the oral care composition of the invention are in the form of a toothpaste or alternatively a mouthrinse. In some embodiments the toothpaste comprises an arginine salt, e.g., arginine hydrochloride, arginine phosphate or arginine bicarbonate.

In some embodiments, the toothpaste optionally comprises one or more of water, an abrasive, a surfactant, a foaming agent, a vitamin, a polymer, an enzyme, a humectant, a thickener, an antimicrobial agent, a preservative, a flavoring, a colorant and/or a combination of two or more thereof.

Some embodiments of the oral care composition of the invention comprise a breath freshener, fragrance or flavoring. Other embodiments comprise an anti-calculus agent. In some embodiments, the anti-calculus agent is a polyphosphate, e.g., pyrophosphate, tripolyphosphate, or hexametaphosphate, e.g., in sodium salt form.

Some embodiments of the invention provide oral care compositions or methods to:
a. reduce or inhibit formation of dental caries,
b. reduce or inhibit demineralization and promote remineralization of the teeth,
c. reduce or inhibit early enamel lesions,
d. reduce or inhibit gingivitis,
e. reduce levels of acid producing bacteria,
f. to increase relative levels of arginolytic bacteria,
g. inhibit microbial biofilm formation in the oral cavity,
h. raise and/or maintain plaque pH at levels of at least about pH 5.5 following sugar challenge,
i. reduce plaque accumulation,
j. whiten teeth,
k. improve whole body health,
l. reduce erosion of the teeth,
m. immunize or protect the teeth against cariogenic bacteria, and/or
n. clean the teeth and oral cavity.

The oral care compositions of the invention also may include an agent to increase the amount of foam that is produced when the oral cavity is brushed.

Illustrative examples of agents that increase the amount of foam include, but are not limited to polyoxyethylene and certain polymers including, but not limited to, alginate polymers.

The polyoxyethylene may increase the amount of foam and the thickness of the foam generated by the oral care carrier component of the oral care composition of the invention. Polyoxyethylene is also commonly known as polyethylene glycol ("PEG") or polyethylene oxide. The polyoxyethylenes suitable for this invention will have a molecular weight of about 200,000 to about 7,000,000. In one embodiment the molecular weight will be about 600,000 to about 2,000,000 and in another embodiment about 800,000 to about 1,000,000. Polyox® is the trade name for the high molecular weight polyoxyethylene produced by Union Carbide.

The polyoxyethylene may be present in an amount of 1 to 90 wt %, in one embodiment 5 to 50 wt % and in another embodiment 10 to 20 wt % by weight of the oral care carrier component of the oral care compositions of the present invention. The dosage of foaming agent in the oral care composition (i.e., a single dose) is about 0.01 to 0.9 wt %, 0.05 to 0.5 wt %, and in another embodiment 0.1 to 0.2 wt %.

The oral care compositions of the invention may also include a flavoring agent. Flavoring agents which are used in the practice of the present invention include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint.

The flavoring agent may be incorporated in the oral composition at a concentration of 0.1 to 5 wt % and 0.5 to 1.5 wt %. The dosage of flavoring agent in the individual oral care composition dosage (i.e., a single dose) is 0.001 to 0.05 wt % and in another embodiment 0.005 to 0.015 wt %.

Sweetening agents which can be used include sucrose, glucose, saccharin, dextrose, levulose, lactose, mannitol, sorbitol, fructose, maltose, xylitol, saccharin salts, thaumatin, aspartame, D-tryptophan, dihydrochalcones, acesulfame and cyclamate salts, in particular sucralose, sodium cyclamate and sodium saccharin, and mixtures thereof. A composition preferably contains from 0.1 to 10 wt % of these agents, preferably from 0.1 to 1 wt %, based on the total composition.

The oral care compositions of the invention also may optionally include one or more chelating agents able to complex calcium found in the cell walls of the bacteria. Binding of this calcium weakens the bacterial cell wall and augments bacterial lysis.

Another group of agents suitable for use as chelating agents in the present invention are the soluble pyrophosphates. The pyrophosphate salts used in the present compositions can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition is generally enough to provide at least about 1.0 wt % pyrophosphate ions, typically from 1.5 to 6 wt %, more typically from 3.5 to 6 wt % of such ions.

Gelled mineral oils are suitable hydrophobic viscosity modifiers. In some embodiments, the gelled mineral oil is preferably a blend of mineral oil and polyethylene, e.g. PLASTIGEL 5, which is a blend of 5% polyethylene in mineral oil, and is available from Pharmaceutical Resources/Lyne Laboratories Inc. of Brockton, Mass. Other suitable plastigels can be prepared in accordance with the teachings of Thau et al., "A New Procedure for the Preparation of Polyethylene-Mineral Oil Gels," J. Soc. Cosmetic Chemists, 16, 359-363 (1965). Suitable hydrophobic viscosity modifiers additional to gelled mineral oils, such as plastigels, can be identified by using the present disclosure as a guide.

The oral care compositions of the invention also optionally include one or more polymers. Polymers can provide certain advantages to the composition, for example when the composition is in the form of a toothpaste or gel, during preparation it is frequently necessary to add some thickening material to provide a desirable consistency of the composition, to provide desirable active release characteristics upon use, to provide shelf stability, and to provide stability of the composition, etc. Typical examples of polymers that can be present in the composition of the invention include polyethylene glycols, polyvinylmethyl ether maleic acid copolymers, polysaccharides (e.g., cellulose derivatives, for example carboxymethyl cellulose, or polysaccharide gums, for example gum karaya, gum arabic, gum tragacanth, xanthan gum or carrageenan gum). Acidic polymers, for example polyacrylate gels, may be provided in the form of their free acids or partially or fully neutralized water soluble alkali metal (e.g., potassium and sodium) or ammonium salts.

Particularly when noncationic antibacterial agents or antibacterial agents, e.g., triclosan, are included in any of the dentifrice components, there is also preferably included from 0.05 to 5 wt % of an agent which enhances the delivery and retention of the agents to, and retention thereof on oral surfaces. Such agents useful in the present invention are disclosed in U.S. Pat. Nos. 5,188,821 and 5,192,531; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 30,000 to about 800,000. These copolymers are available for example as Gantrez. e.g., AN 139 (M.W. 500,000), AN 119 (M.W. 250,000) and preferably S-97 Pharmaceutical Grade (M.W. 700,000) available from ISP Technologies, Inc., Bound Brook, N.J. 08805. The enhancing agents when present are present in amounts ranging from 0.05 to 3 wt %.

A particular class of thickening or gelling agents includes a class of homopolymers of acrylic acid crosslinked with an alkyl ether of pentaerythritol or an alkyl ether of sucrose, or carbomers. Orally acceptable carbomers are commercially available from B. F. Goodrich.

In certain embodiments, thickening agents in an amount of 0.1 to 15.0 wt % by weight of the total composition are used, in another embodiment from 0.5 to 8 wt %, in another embodiment from 0.5 to 5 wt %.

In addition to the above described components, the embodiments of this invention can contain a variety of optional dentifrice ingredients some of which are described below. Optional ingredients include, for example, but are not limited to, adhesives, sudsing agents, flavoring agents, sweetening agents, additional antiplaque agents, abrasives, and coloring agents.

The compositions of the invention can be made using methods which are common in the oral product area.

As used throughout, ranges are used as shorthand for describing each and every value that is within the range. Any value within the range can be selected as the terminus of the range. In addition, all references cited herein are hereby incorporated by reference in their entireties.

In the event of a conflict in a definition in the present disclosure and that of a cited reference, the present disclosure controls. It is understood that when formulations are described, they may be described in terms of their ingredients, as is common in the art, notwithstanding that these ingredients may react with one another in the actual formulation as it is made, stored and used, and such products are intended to be covered by the formulations described.

The following examples further describe and demonstrate illustrative embodiments within the scope of the invention. The examples are given solely for illustration and are not to be construed as limitations of this invention as many variations are possible without departing from the scope thereof.

Various modifications of the invention in addition to those shown and described herein should be apparent to those skilled in the art and are intended to fall within the appended claims.

EXAMPLES

Aluminum Chlorohydrate Production

EACH made by Glycine

An aqueous solution of 0.5M AlC13.6H20 (50 mmol) was buffered with 1.23M glycine (123 mmol) and heated to 95° C. under vigorous stirring. To this solution, a 1 N Ca(OH)2 (61.5 mmol) was added dropwise over a 2 hour 30 minute period until a final molar ratio of OH:Al of 2.46 was achieved.

EACH made by Arginine 18.81 mmol $AlCl_3.6H_2O$ is buffered with 23.136 mmol L-arginine in 29 ml deionized water, held at 95° C. in a glass reactor and stirred vigorously. To this solution, 9 ml $Ca(OH)_2$ (12.08 mmol) suspension is added dropwise over a 2 hour period. The reaction solution is left heated and stirring for an additional 1 hour.

Example 1

To determine the effectiveness of aluminum chlorohydrate (ACH) to at least partially occlude dentin tubules, by at least partially reducing fluid movement within the dentin tubules, dentin disks were prepared. Each dentin disk was obtained by cutting a disk from an extracted human molar tooth. Each disk was etched for 45 seconds in a 6 wt % aqueous solution of citric acid to expose the dentin tubules, and subsequently sonicated for a period of 30 minutes in deionized water to open up the dentin tubules. Each disk was immersed in a phosphate buffer solution (PBS) which contained salts present in human saliva, and subjected to constant shaking for an overnight period.

Using a Flodec hydraulic conductance device, available from de Marco Engineering, Geneva, Switzerland, in vitro hydraulic conductance measurements were carried out to determine fluid flow through the dentin tubules of the disks.

A baseline flow rate was measured by measuring the flow of a 400 μL volume of PBS for a period of 10 minutes through the dentin tubules of the disks.

Thereafter, the disks were treated for a period of 2 minutes with a mixture comprising (i) a 200 μL volume of aluminum chlorohydrate which was present in an amount to provide 0.5 wt % aluminum in an anhydrous carrier comprising a C6 to C12 fatty acid ester of glycerol, hereinafter called a medium chain triglyceride (MCT) and (ii) a 200 µL volume of saliva. Subsequently, the dentin disks were rinsed twice with a 400 µL volume of fresh saliva.

The flow rate was measured after this single treatment (two successive treatments to mimic a single day's treatment) with the aluminum chlorohydrate.

The measured flow rate was compared to the baseline flow rate and a % reduction in flow rate as a result of the single treatment with the aluminum chlorohydrate was calculated. The resultant % reduction in flow rate is shown in Table 1. There was a 94% reduction in fluid flow through the dentine tubules as a result of occlusion of the dentin tubules by the aluminum chlorohydrate.

TABLE 1

|  | Treatment | Average % Reduction in Fluid Flow |
|---|---|---|
| Example 1 | 0.5 wt % Al in ACH/glycine in MCT | 95.5 |
| Comparative Example 1 | 0.5 wt % Al in ACH/arginine in MCT | 2 |
| Comparative Example 2 | 0.5 wt % Al in ACH in MCT | 35.5 |
| Comparative Example 3 | 2 wt % Zr in zirconium/glycine (ZG) in MCT | 74.5 |

Example 2

Example 1 was repeated and the resultant % reduction in flow rate is also shown in Table 1, together with an average % reduction.

It may be seen from Examples 1 that a significant, average 95.5%, reduction in fluid flow through the dentin tubules was achieved. This shows that the aluminum chlorohydrate produced using the glycine buffer is an effective dentin tubule occluding agent.

Comparative Example 1

It may be seen from Comparative Example 1 (EACH made by Arginine) that a substantially negligible, average 2%, reduction in fluid flow through the dentin tubules was achieved. This shows that the aluminum chlorohydrate produced using an arginine buffer is not an effective dentin tubule occluding agent.

Comparative Example 2

In Comparative Examples 2, the testing protocol of Examples was repeated, but the test was carried out on an aluminum chlorohydrate (ACH) produced in the absence of any buffer instead of the aluminum chlorohydrate produced using a glycine buffer of Example 1. The ACH employed was an aluminum chlorohydrate available from Summit under the trade name Reach 103.

It may be seen that commercial ACH has an average 35.5%, reduction in fluid flow through the dentin tubules was achieved. This shows that the conventional aluminum chlorohydrate produced in the absence of any buffer is not a particularly effective dentin tubule occluding agent.

Comparative Example 3

The zirconium glycine (ZG) as another control was prepared following a procedure outlined in U.S. Pat. No. 7,897,799 and Pappas I., et al., *Crystal Growth & Design,* 2009 (9):5213-5219. The zirconium glycine was suspended in the medium chain triglyceride (MCT) to prepare a 2 wt % ZG suspension.

It may be seen from Comparative Example 3 that a reduced, as compared to Example 1, average 74.5%, reduction in fluid flow through the dentin tubules was achieved. This shows that the aluminum chlorohydrate produced using a glycine buffer is a more effective dentin tubule occluding agent than zirconium glycine as disclosed in the Applicant's prior application PCT/US2011/66496.

These results of Example 1 and Comparative Examples 1 to 3 indicate that ACH synthesized with a glycine buffer and suspended in a hydrophobic anhydrous carrier such as a C6-C12 fatty acid triglyceride can significantly reduce fluid movement within dentin tubules. The ACH synthesized with a glycine buffer showed a superior reduction in fluid movement within dentin tubules as compared to ACH. The inferior performance of ACH in Comparative Examples 3 was not expected since it was known that such ACH is effective as an antiperspirant active by a mechanism in which sweat glands are plugged by the ACH. Furthermore, a comparison of Example 1 which employed glycine and Comparative Example 2 which employed an arginine buffer suggests that the selection of the amino acid buffer is important in achieving effective dentin tubule occlusion.

We claim:

1. An oral care composition comprising:
   an effective amount of aluminum chlorohydrate suspended in a carrier for preventing, reducing or inhibiting dentinal hypersensitivity;
   wherein the aluminum chlorohydrate has an aluminum to chloride molar ratio of from about 0.5:1 to about 3:1, and
   wherein the aluminum chlorohydrate exhibits a size exclusion chromatography ("SEC") chromatogram having an SEC Peak 4 to Peak 3 intensity ratio of at least 7:1, and an SEC Peak 4 intensity greater than an SEC Peak 5 intensity.

2. The composition of claim 1, wherein the composition is substantially anhydrous.

3. The composition of claim 1, wherein the carrier is hydrophobic.

4. The composition claim 3, wherein the hydrophobic carrier comprises an ingredient selected from: a fatty acid ester of glycerol; an oil selected from a vegetable oil, a synthetic oil or a mineral oil; a wax; a silicone oil or fluid; an alkylene glycol; a polyalkylene glycol; and a combination of two or more thereof.

5. The composition of claim 3, wherein the hydrophobic carrier comprises a $C_{6-12}$ fatty acid ester of glycerol.

6. The composition of claim 1, further comprising at least one buffer selected from glycine and betaine.

7. The composition of claim 1, wherein the aluminum chlorohydrate is present in an amount of from 0.01 wt. % to 20 wt. % of a total weight of the composition.

8. The composition of claim 1, wherein the aluminum chlorohydrate has an SEC Peak 4 area of at least 50% of a total area of Peaks 1, 2, 3, 4, 5, and 6 in the SEC chromatogram.

9. The composition of claim 1, wherein the aluminum chlorohydrate has an SEC Peak 3 area of less than about 10% of a total area of Peaks 1, 2, 3, 4, 5, and 6 in the SEC chromatogram.

10. The composition of claim 1, wherein the aluminum chlorohydrate has an SEC Peak 5 area of less than about 30% of a total area of Peaks 1, 2, 3, 4, 5, and 6 in the SEC chromatogram.

11. The composition of claim 1, wherein the aluminum chlorohydrate has an SEC Peak 1 area of less than about 10% of a total area of Peaks 1, 2, 3, 4, 5, and 6 in the SEC chromatogram, and an SEC Peak 2 area of less than about 10% of the total area of Peaks 1, 2, 3, 4, 5, and 6 in the SEC chromatogram.

12. The composition of claim 1, wherein the aluminum chlorohydrate has an SEC Peak 4 area of 95% to 100% of a total area of Peaks 1, 2, 3, 4, 5, and 6 in the SEC chromatogram, no SEC Peak 3 area in the SEC chromatogram, and no SEC Peak 5 area in the SEC chromatogram.

13. The composition of claim 1, wherein the composition is a mouthrinse, a mouthwash, or a toothpaste.

14. A method of preventing, reducing or inhibiting dentinal hypersensitivity, the method comprising:
applying an effective amount of the composition of claim 1 to an oral cavity of a subject in need thereof.

15. A method of occluding dentin tubules, the method comprising administering the composition of claim 1 to a subject in need thereof.

16. An oral care care composition, comprising:
an effective amount of aluminum chlorohydrate suspended in a carrier for preventing, reducing, or inhibiting dentinal hypersensitivity;
wherein the aluminum chlorohydrate is formed from an aluminum salt, a buffer comprising glycine or betaine, and an inorganic base, and
wherein the aluminum chlorohydrate exhibits a size exclusion chromatography ("SEC") chromatogram having an SEC Peak 4 to Peak 3 intensity ratio of at least 7:1, and an SEC Peak 4 intensity greater than an SEC Peak 5 intensity.

17. The composition of claim 16, wherein the aluminum chlorohydrate has an aluminum to chloride molar ratio of about 0.3:1.

18. The composition of claim 16, wherein the aluminum chlorohydrate has an aluminum to chloride molar ratio of about 0.4:1.

19. An oral care composition, comprising:
an effective amount of aluminum chlorohydrate suspended in a carrier for preventing, reducing, or inhibiting dentinal hypersensitivity;
wherein the aluminum chlorohydrate is formed from an aqueous solution of an aluminum salt, a buffer, and in inorganic base, so that the aqueous solution has an OH:Al molar ratio of about 2:1 to about 2.6:1, and
wherein the aluminum chlorohydrate exhibits a size exclusion chromatography ("SEC") chromatogram having an SEC Peak 4 to Peak 3 intensity ratio of at least 7:1, and an SEC Peak 4 intensity greater than an SEC Peak 5 intensity.

20. The composition of claim 19, wherein the buffer comprises glycine.

21. The composition of claim 19, wherein the buffer comprises betaine.

* * * * *